US006918893B2

(12) United States Patent
Houde et al.

(10) Patent No.: US 6,918,893 B2
(45) Date of Patent: Jul. 19, 2005

(54) MULTIPLE PORT FLUID CONTROL VALVES

(75) Inventors: Eric Houde, Saratoga Springs, NY (US); Mark van Diver, Argyle, NY (US); Scott Diamond, Fort Edwards, NY (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/263,018

(22) Filed: Oct. 2, 2002

(65) Prior Publication Data

US 2003/0125673 A1 Jul. 3, 2003

Related U.S. Application Data

(60) Provisional application No. 60/326,941, filed on Oct. 4, 2001.

(51) Int. Cl.[7] .................................................. A61M 5/00
(52) U.S. Cl. .......................................... 604/248; 604/32
(58) Field of Search ............................. 604/30, 32, 35, 604/118, 82, 248, 290, 902, 93.01, 258

(56) References Cited

U.S. PATENT DOCUMENTS

| | | | |
|---|---|---|---|
| 3,384,372 A | 5/1968 | Dickens | |
| 4,430,074 A | 2/1984 | Mooring | |
| 4,489,721 A | * 12/1984 | Ozaki et al. ........... | 128/205.24 |
| 4,512,764 A | 4/1985 | Wunsch | |
| 4,559,036 A | 12/1985 | Wunsch | |
| 4,604,093 A | 8/1986 | Brown et al. | |
| 4,789,000 A | 12/1988 | Aslanian ..................... | 137/556 |
| 4,790,193 A | 12/1988 | Moriuchi et al. ............. | 73/756 |
| 4,819,653 A | 4/1989 | Marks | |
| 4,915,688 A | 4/1990 | Bischof et al. ................ | 604/83 |
| 5,020,562 A | 6/1991 | Richmond et al. | |
| 5,074,334 A | 12/1991 | Onodera ................ | 137/625.41 |
| 5,084,031 A | 1/1992 | Todd et al. .................. | 604/248 |
| 5,104,387 A | 4/1992 | Pokorney et al. | |
| 5,168,901 A | 12/1992 | Marks | |
| 5,171,216 A | 12/1992 | Dasse et al. | |
| 5,288,290 A | 2/1994 | Brody | |
| 5,324,274 A | 6/1994 | Martin | |
| 5,354,267 A | * 10/1994 | Niermann et al. ............. | 604/32 |
| 5,356,375 A | 10/1994 | Higley ........................ | 604/30 |
| 5,378,229 A | 1/1995 | Layer et al. | |
| 5,399,172 A | 3/1995 | Martin et al. | |
| 5,562,614 A | 10/1996 | O'Donnell .................... | 604/65 |
| 5,601,651 A | 2/1997 | Watabe | |
| 5,640,995 A | 6/1997 | Packard et al. .............. | 137/597 |
| 5,730,731 A | 3/1998 | Mollenauer et al. ......... | 604/246 |
| 5,800,383 A | 9/1998 | Chandler et al. ............. | 604/35 |
| 5,806,519 A | 9/1998 | Evans, III et al. .......... | 128/654 |
| 5,830,180 A | 11/1998 | Chandler et al. ............. | 604/65 |
| 5,840,026 A | 11/1998 | Uber, III et al. ............ | 600/431 |
| 6,063,052 A | 5/2000 | Uber, III et al. .............. | 604/32 |
| 6,083,205 A | 7/2000 | Bourne et al. | |
| 6,110,144 A | 8/2000 | Choh et al. .............. | 604/99.01 |
| 6,238,372 B1 | 5/2001 | Zinger et al. ............... | 604/246 |

* cited by examiner

Primary Examiner—Manuel Mendez
(74) Attorney, Agent, or Firm—Marshall, Gerstein & Borun LLP

(57) ABSTRACT

A fluid control valve is disclosed which, with a single valve, can manipulate flow between a saline supply, a contrast supply, a waste dump and a catheter. The control valve includes three primary positions including a contrast position where the valve provides communication between an injector and a contrast supply while isolating the saline supply and catheter. The valve also can be moved to a saline/waste position where the valve provides communication between the injector and the saline supply and/or the waste dump while isolating the contrast supply and catheter. The valve also can be moved to an injection position where the valve provides communication between the injector and the catheter. A single valve provides all three functions. The valve also may provide communication between a pressure transducer and catheter during the saline loading, waste dumping and contrast loading functions. The valve also provides protection or isolation of the pressure transducer during injection procedures.

11 Claims, 13 Drawing Sheets

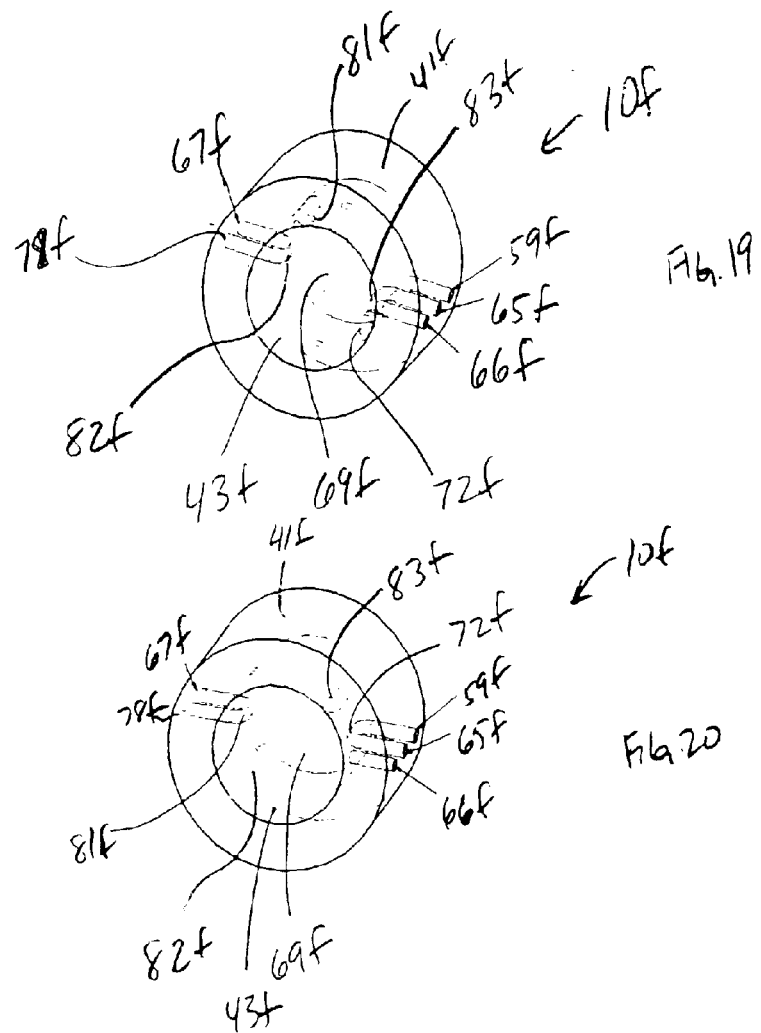
FIG. 19
FIG. 20
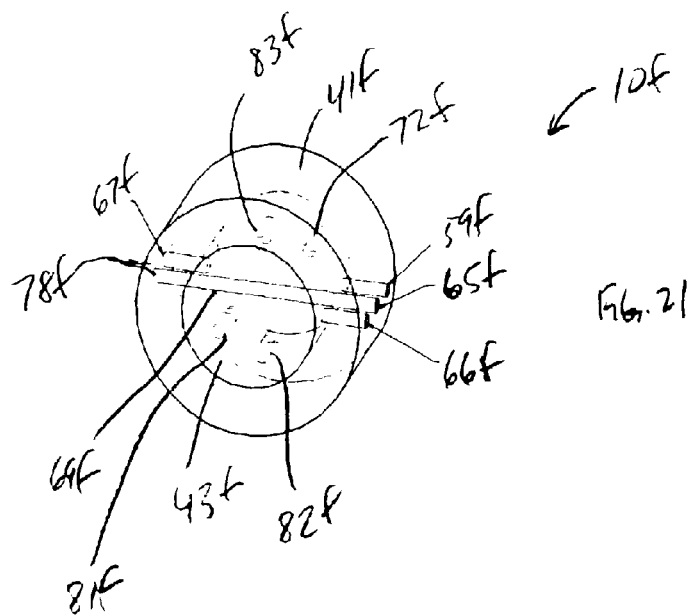
FIG. 21

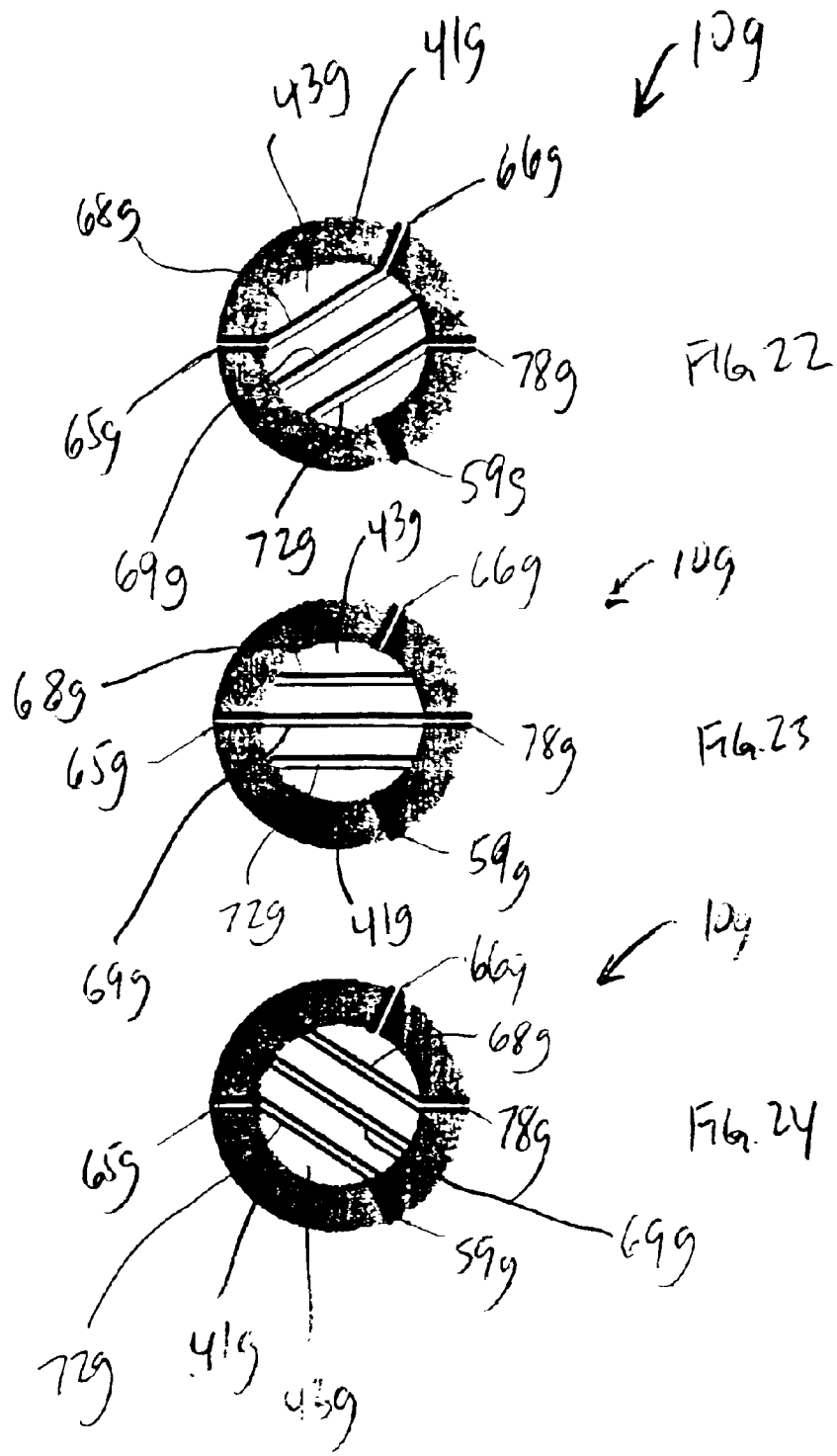

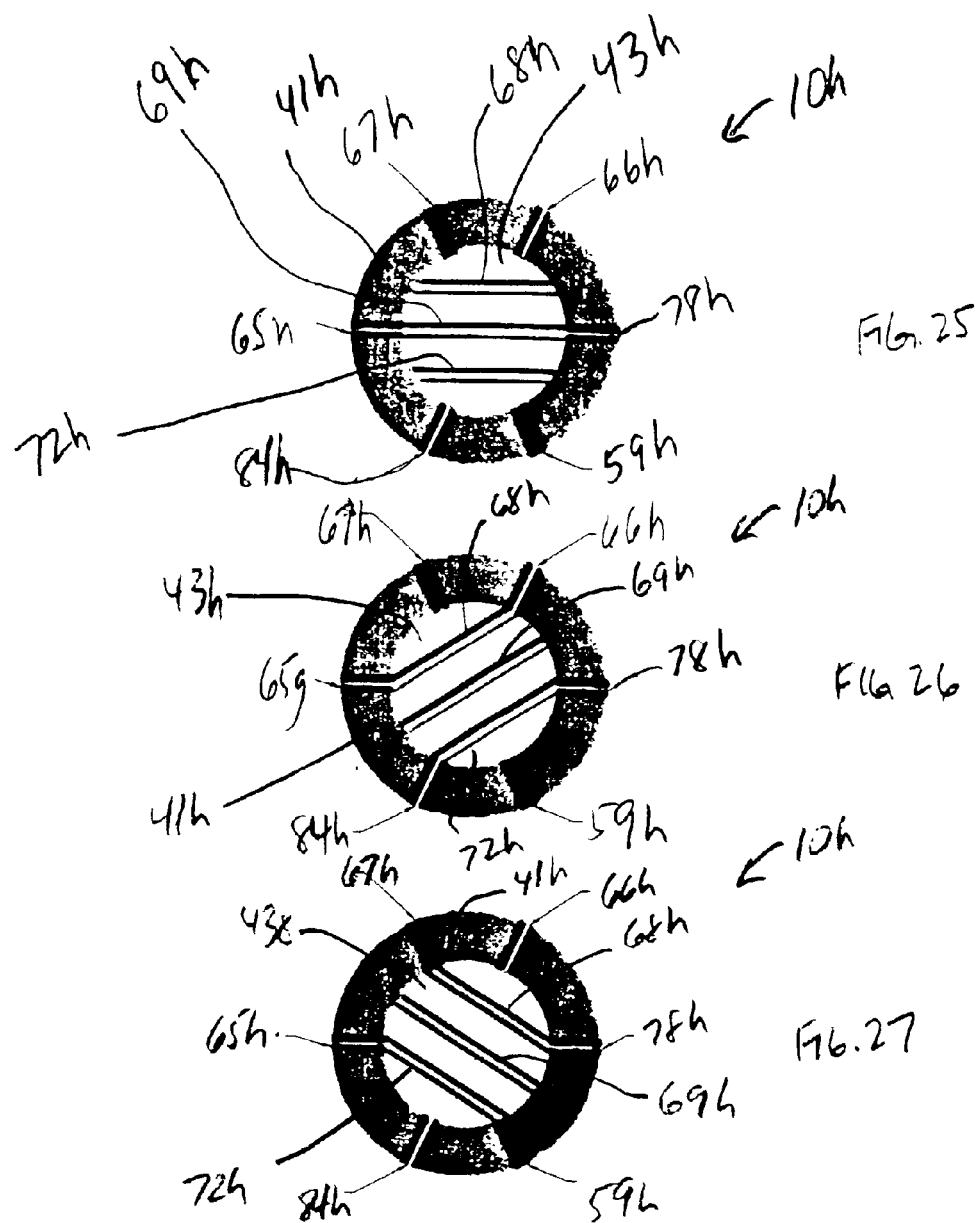

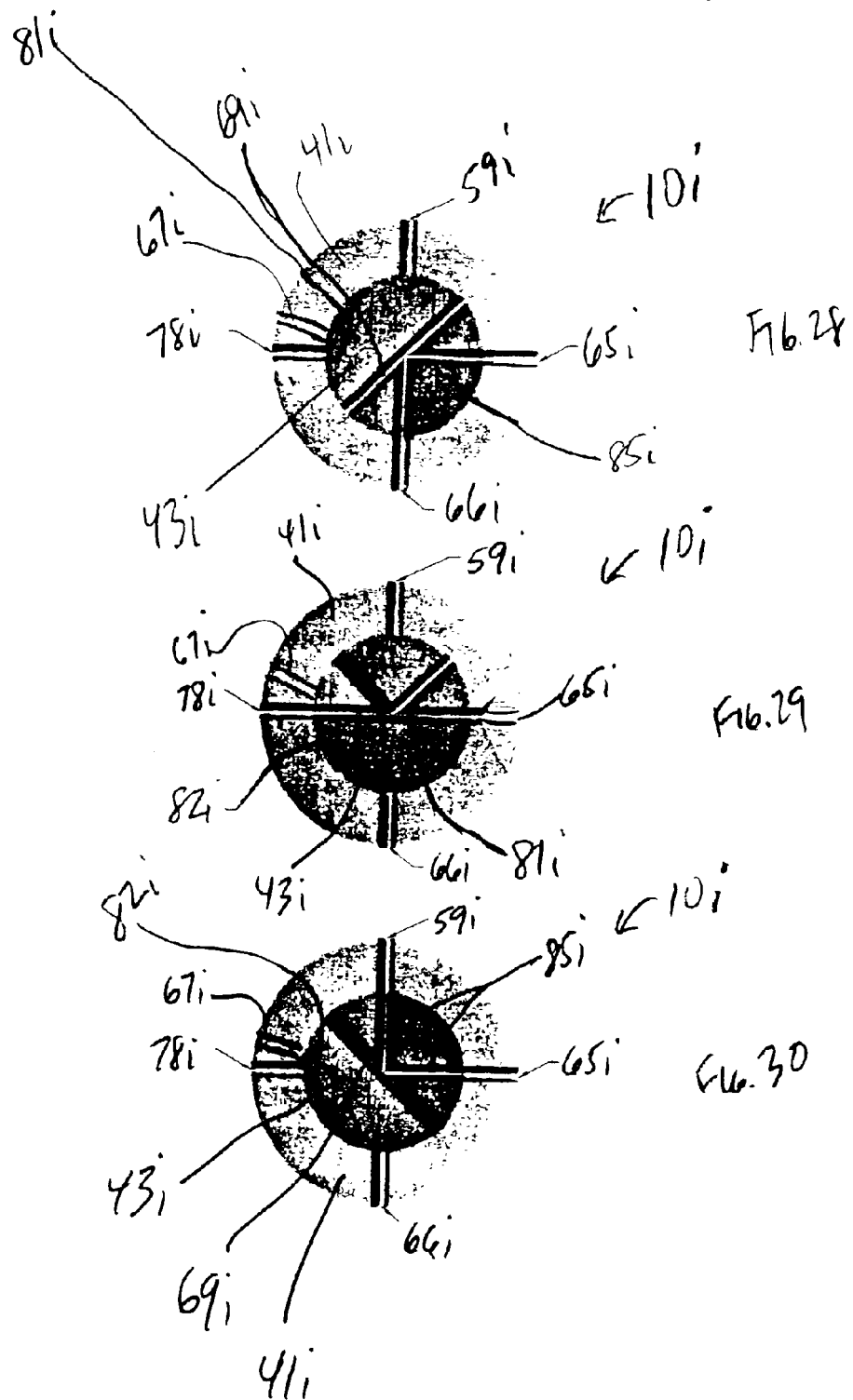

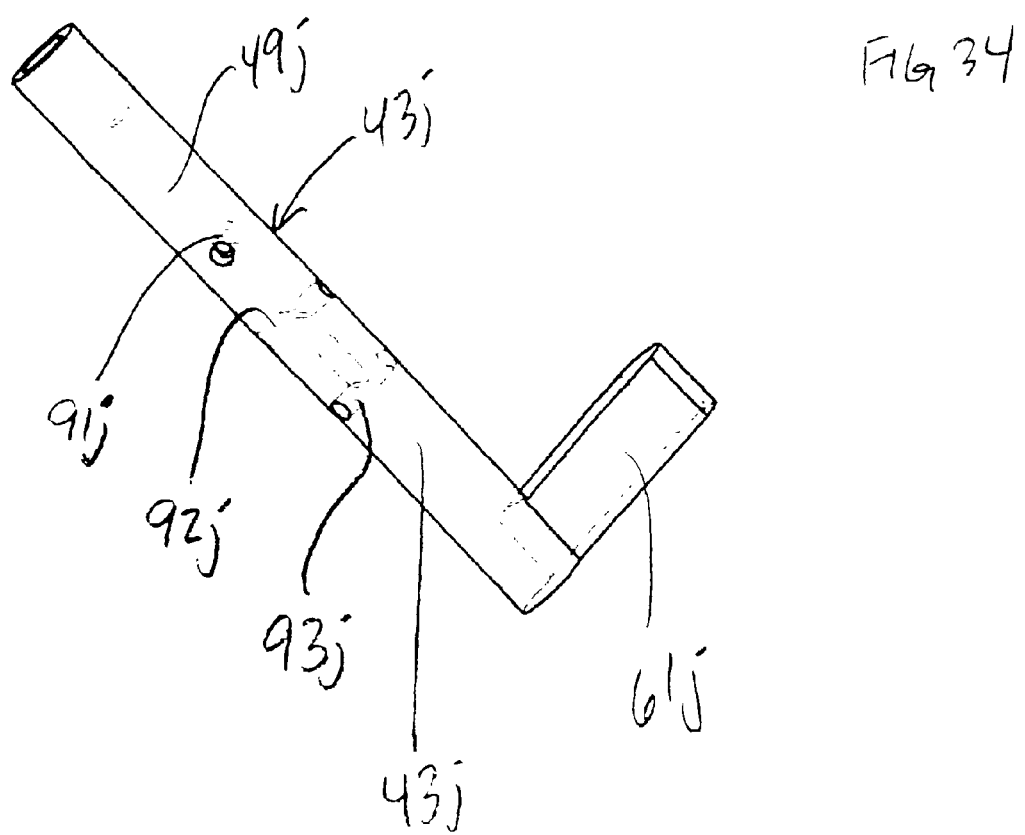

MULTIPLE PORT FLUID CONTROL VALVES

CROSS-REFERENCE TO RELATED APPLICATION

This application claims the benefit under 35 U.S.C. §119 (e) of U.S. provisional patent application Ser. No. 60/326,941 filed Oct. 4, 2001, the disclosure of which is incorporated herein by reference.

TECHNICAL FIELD

A fluid control valve is disclosed. More specifically, a fluid control valve that selectively controls a flow of fluid between multiple input and output ports and that selectively provides communication between a pressure transducer port and an output port and that selectively isolates the pressure transducer port is disclosed. The disclosed fluid control valve is used to control various fluids injected during intravascular medical procedures. More specifically, the disclosed fluid control valve facilitates the control and injection of contrast and saline solutions during an intravascular procedure.

BACKGROUND OF THE RELATED ART

Various medical procedures involve the introduction of fluids into the body of a patient using a catheter. When a series of different fluids are to be administered, it is often necessary to flush one fluid from the catheter before the next fluid is administered. For example, during angioplasty, the catheter is often flushed with saline before and/or after the addition of contrast solution. Further, it is also necessary to purge any injection lines of air and to prevent the reintroduction of air into the lines.

Accordingly, it is often necessary to selectively connect a catheter to any one of a number of fluid sources such as a contrast solution source, saline source and a waste dump. Further, it is often necessary to connect the catheter to a pressure transducer to monitor the intravascular pressure during a procedure.

The most commonly used apparatus for these types of procedures involves the connection of a catheter to a manifold which consists of a plurality of stopcock valves connected in a series. While one of the stopcocks is connected to the catheter, the other stopcocks are connected to fluid supplies, a pressure transducer, an injection mechanism or other equipment. The physician is required to selectively open and close the stopcock valves during the procedure.

Because a physician is required to manipulate a number of stopcock valves during a procedure to achieve a desired flow path to or from the catheter, it takes a considerable degree of training to learn how to properly operate one of the prior art manifolds. Further, because it is not immediately evident from looking at the manifold which way the fluid is flowing, it is easy to make an improper connection resulting in a high-pressure fluid being applied to a pressure transducer, causing damage or malfunction of the transducer.

Further, because these so-called stopcock manifolds include a large number of moving parts, they are expensive to manufacture. Still further, because a number of stopcock valves are involved in one of these manifolds, the handles must be small so as to not cause interference with one another. However, the small handles can be difficult to grasp and manipulate.

As a result, there is a need for an improved manifold system which involves fewer moving parts and which is easier for the physician to manipulate.

SUMMARY OF THE DISCLOSURE

A fluid control valve with controlling fluid flow between a catheter, a saline supply, a waste dump, a contrast supply and an injector is disclosed. In an embodiment, a single valve means movable to at least three rotational positions is disclosed. The three rotational positions include a contrast position where the valve means provides communication between the injector and contrast supply while isolating the saline supply, a saline/waste position where the valve means provides communication between the injector and the saline supply and the waste dump while isolating the contrast supply, and an injection position where the valve means provides communication between the injector and the catheter while isolating the contrast supply.

In a further refinement, a fluid control valve for controlling fluid flow between a catheter, a saline supply, a waste dump, a contrast supply, a pressure transducer and an injector is disclosed. In this refinement, the control valve comprises a single valve means movable to at least three rotational positions including a contrast position where the valve means provides communication between the injector and the contrast supply while isolating the saline supply and while isolating the catheter and pressure transducer from the injector while providing communication between the catheter and the pressure transducer, a saline/waste position where the valve means provides communication between the injector and the saline supply and the waste dump while isolating the contrast supply and while isolating the catheter and pressure transducer from the injector but providing communication between the catheter and the pressure transducer, and an injection position where the valve means provides communication between the injector and the catheter while isolating the pressure transducer, contrast supply and waste dump.

In yet another refinement, a fluid control valve is disclosed for controlling fluid between the catheter, a saline supply, a waste dump, a contrast supply, a pressure transducer and an injector. The control valve comprises a single valve means movable to at least three rotational positions including a contrast position where the valve means provides communication between the injector and the contrast supply while isolating the saline supply and while isolating the catheter and pressure transducer from the injector but providing communication between the catheter and pressure transducer, a waste position where the valve means provides communication between the injector and the waste dump while isolating the contrast supply and while isolating the catheter and pressure transducer from the injector but providing communication between the catheter and pressure transducer and an injection position where the valve means provides communication between the injector, the saline supply and the catheter while isolating the pressure transducer, contrast supply and waste dump.

In another refinement, a fluid control valve is disclosed for controlling fluids between a catheter, a saline supply, a waste dump, a contrast supply and an injector. The fluid control valve comprises a valve body comprising a cylindrical bore and an outer surface. The valve body further comprises a plurality of passages providing communication between the cylindrical bore and the outer surface. The plurality of passages comprises at least one output passage connected to the catheter, a contrast input passage connected to the contrast supply, at least one saline/waste input/output passage connected to the saline supply and the waste dump, and at least one injector passage connected to the injector. A cylindrical valve stem is rotatably disposed within the cylindrical bore. The valve stem has a central axis. The valve stem further comprises at least one connecting passage extending through the valve stem. The connecting passage selectively connects or provides communication between the injector passage in at least one of the output passage, the contrast input passage and the saline/waste input/output passage, depending upon a rotational position of the valve stem. The valve stem is rotatable within the cylindrical bore to at least three rotatable positions. Those rotatable positions include a contrast position where the connecting of the valve stem provides communication between the injector passage and the contrast input passage, the saline/waste position where the connecting passage provides communication between the injector passage and the saline/waste input/output passage and an injection position where the connecting passage provides communication between the injector passage and the output passage.

In a further refinement, the at least output passage of the valve body comprises two output passages connected to the catheter that include a contrast output passage and a saline output passage. The valve body further comprises a waste input passage. The at least one saline/waste input/output passage of the valve body further comprises a separate saline input passage and a separate waste output passage. The at least one injector passage comprises a contrast injector passage, a saline injector passage and a waste injector passage. The valve stem further comprises a linking passage that extends from the connecting passage and out through the valve stem. In the contrast position, the connecting passage provides communication between the contrast injector passage and the contrast output passage. A linking passage provides communication between the contrast input passage and the connecting passage. In the injection position, the connecting passage provides communication between the saline injector passage and the saline output passage. The linking passage provides communication between the connecting passage and the saline input passage. In the saline/waste position, the connecting passage provides communication between the waste input passage the waste injector passage and the linking passage provides communication between the connecting passage and the waste output passage.

In a further refinement, a waste input passage is connected to a waste input line which connects the waste input passage to the catheter. The waste input line comprises a one-way check valve permitting flow from the catheter to the waste input passage and not vice versa. The saline output passage is connected to a saline output line which connects the saline output passage to the catheter. The saline output line comprises a one-way check valve permitting flow from the saline output passage to the catheter and not vice versa. The contrast output passage is connected to a contrast output line which connects the contrast output passage to the catheter. The contrast output line comprises a one-way check valve permitting flow from the contrast output passage to the catheter and not vice versa.

In a further refinement, the saline input passage is connected to saline input line which connects the saline input line passage to the saline supply. The saline input line comprises a one-way check valve permitting flow from the saline supply to the saline input passage and not vice versa. The contrast input passage is connected to a contrast input line which connects the contrast input passage to the contrast supply. The contrast input line comprises a one-way check valve permitting flow from the contrast supply to the contrast input passage and not vice versa. A waste output passage is connected to a waste output line which connects the waste output passage to the waste dump. The waste output line comprises a one-way check valve permitting flow from the waste output passage to the waste dump and not vice versa.

In another refinement, the saline/waste input/output passage is connected to both a saline input line and waste output line. The saline input line connects the saline/waste input/output passage to the saline supply. The saline input line comprises a one-way check valve permitting flow from the saline supply to the saline/waste input/output passage and not vice versa. The waste output line connects the saline/waste input/output passage to the waste dump. The waste output line comprises a one-way check valve which permits flow from the saline/waste input/output passage to the waste dump and not vice versa.

In another refinement, the at least one connecting passage of the valve stem comprises a saline/waste connecting passage, an injector connecting passage and a contrast connecting passage. In the contrast position, the contrast connecting passage provides communication between the injector passage and the contrast input passage. In the saline/waste position, the saline/waste connecting passage provides communication between the injector passage and the contrast input passage. In the saline/waste position, the saline/waste connecting passage provides communication between the injector passage and the saline/waste input/output passage. In the injecting position, the injector connecting passage provides communication between the injector passage and the output passage.

In a further refinement of the above concept, the valve body further comprises a first pressure transducer passage in a second pressure transducer passage. In the contrast position, the saline/waste connecting passage provides communication between the output passage and the first pressure transducer passage. In the saline/waste position, the contrast connecting passage provides communication between the output passage and the second pressure transducer passage.

In still a further refinement of the above concept, the valve stem further comprises a first linking passage that extends from a contrast connecting passage axially along the valve stem and out through the valve stem. The contrast connecting passage comprises a first end and a second end. The valve stem further comprises a second linking passage that extends from the saline/waste connecting passage axially along the valve stem and out through the valve stem. The saline/waste connecting passage comprises a first end and a second end. The valve body further comprises a pressure transducer passage providing communication between the cylindrical bore and a pressure transducer. In the contrast position, the contrast position passage provides communication between the injector passage and the contrast input passage and the first linking passage provides communication between the pressure transducer passage and the output passage. In the saline/waste position, the saline/waste connecting passage provides communication between the injector passage and the saline/waste input/output passage and the second linking passage provides communication between the pressure transducer and the output passage. In the injection position, the injector connecting passage provides communication between the injector passage and the output passage and the pressure transducer passage is blocked by the valve stem.

In a further refinement, the saline/waste input/output passage, the output passage, the injector passage and the contrast input passage are coplanar.

In a further refinement, the valve body further comprises a waste input passage. The at least one saline/waste input/ output passage with the valve body comprising a separate saline input passage and a separate waste output passage. The at least one injector passage comprises a combination contrast/saline injector passage and a waste injector passage. The valve stem further comprises a linking passage the extends from the connecting passage along the valve stem and out through the valve stem. In the contrast position, the connecting passage provides communication between the combination contrast/saline injector passage and the output passage and, in this contrast position, the linking passage provides communication between the contrast input passage and the connecting passage. In the injection position, the connecting passage provides communication between the combination contrast/saline injector passage and the output passage and, in this injection position, the linking passage provides communication between the connecting passage and the saline input passage. In the saline/waste position, the connecting passage provides communication between the waste input passage and the waste injector passage and the linking passage provides communication between the connecting passage and the waste output passage.

In the above refinement, the saline input passage, the output passage, the combination contrast/saline injector passage and the contrast input passage are coplanar.

In another refinement, the at least one output passage of the valve body comprises a combination input/output passage through which saline and contrast passes towards the catheter and through which waste passes from the catheter. The valve body further comprises a pressure transducer passage. The at least one connecting passage comprises a catheter connecting passage, a contrast connecting passage, a saline/waste connecting passage and a pressure transducer connecting passage. In the contrast position, the contrast connecting passage provides communication between the contrast input passage and the injector passage and the pressure transducer connecting passage provides communication between the combination input/output passage and the pressure transducer passage. In the injection position, the catheter connecting passage provides communication between the injector passage and the combination input/output passage and the pressure transducer passage is blocked by the valve stem. In the saline/waste position, the saline/waste connecting passage provides communication between the saline/waste input/output passage and the injector passage and the pressure transducer connecting passage provides communication between the combination input/output passage and the pressure transducer passage.

In the above refinement, the combination input/output passage, pressure transducer passage, saline/waste input/output passage and the injector passage are coplanar.

In another refinement of the above concept, the combination input/output passage, the pressure transducer passage, the saline/waste input/output passage, the injector passage and the contrast input passage are coplanar.

In another refinement, the at least one connecting passage comprises an injector connecting passage and a combination saline/waste/contrast connecting passage. In the contrast position, the combination saline/waste/contrast connecting passage provides communication between the contrast input passage and the injector passage. In the injection position, the injector connecting passage provides communication between the injector passage and the output passage. And, in the saline/waste position, the combination saline/waste/contrast connecting passage provides communication between the saline/waste input/output passage and the injector passage.

In another refinement of the above concept, the valve stem further comprises a first linking passage in a second linking passage and the valve body further comprises a pressure transducer port. In the contrast position, the first linking passage provides communication between the output passage and the pressure transducer passage. In the injection position, the pressure transducer passage is blocked by the valve stem. In the saline/waste position, the second linking passage provides communication between the output passage and the pressure transducer passage.

In another refinement, the at least one output passage of the valve body comprises two output passages connected to the catheter including a contrast output passage and a saline output passage. The valve body further comprises a waste input passage. The at least one saline/waste input/output passage of the valve body comprises a separate saline input passage and a separate waste output passage. The connecting passage of the valve stem extends axially along the valve stem. The valve stem further comprises a contrast linking passage that extends transversely through the connecting passage and through the valve stem. The valve stem also includes a saline linking passage that extends transversely through the connecting passage and through the valve stem. Further, the valve stem further includes a waste linking passage which extends transversely through the connecting passage through the valve stem. In the contrast position, the connecting and contrast linking passages provide communication between the injector passage, the contrast input passage and the contrast output passage. In the contrast position, the saline and waste linking passages are blocked by the valve body. In the injection position, the connecting and saline linking passages provide communication between the injector passage, the saline output passage and the saline input passage. In the injection position, the contrast and waste linking passages are blocked by the valve body. In the saline/waste position, the connecting and waste linking passages provided communication between the injector passage, the waste input passage and the waste output passage. In the saline/waste position, the saline and contrast linking passages are blocked by the valve body.

BRIEF DESCRIPTION OF THE DRAWINGS

FIG. 19 is a perspective view of yet another fluid control valve in accordance with the disclosure;

FIG. 20 is another perspective view of the fluid control valve shown in FIG. 19, but in a different rotational position;

FIG. 21 is another perspective view of the fluid control valve shown in FIG. 19 but in yet another different rotational position;

FIG. 22 is an end sectional view of yet another fluid control valve in accordance with the disclosure;

FIG. 23 is another end sectional view of the fluid control valve shown in FIG. 22, but in a different rotational position;

FIG. 24 is another end sectional view of the fluid control valve shown in FIG. 22, but in yet another different rotational position;

FIG. 25 is an end sectional view of yet another fluid control valve in accordance with the disclosure;

FIG. 26 is another end sectional view of the fluid control valve shown in FIG. 25, but in a different rotational position;

FIG. 27 is another end sectional view of the fluid control valve shown in FIG. 25, but in yet another different rotational position;

FIG. 28 is an end sectional view of yet another fluid control valve in accordance with the disclosure;

FIG. 29 is another end sectional view of the fluid control valve shown in FIG. 28, but in a different rotational position;

FIG. 30 is another end sectional view of the fluid control valve shown in FIG. 28, but in yet another different rotational position;

FIG. 34 is a perspective view of the handle/valve stem of the fluid control valve shown in FIG. 31.

DETAILED DESCRIPTION OF THE PRESENTLY PREFERRED EMBODIMENTS

Figure 1:
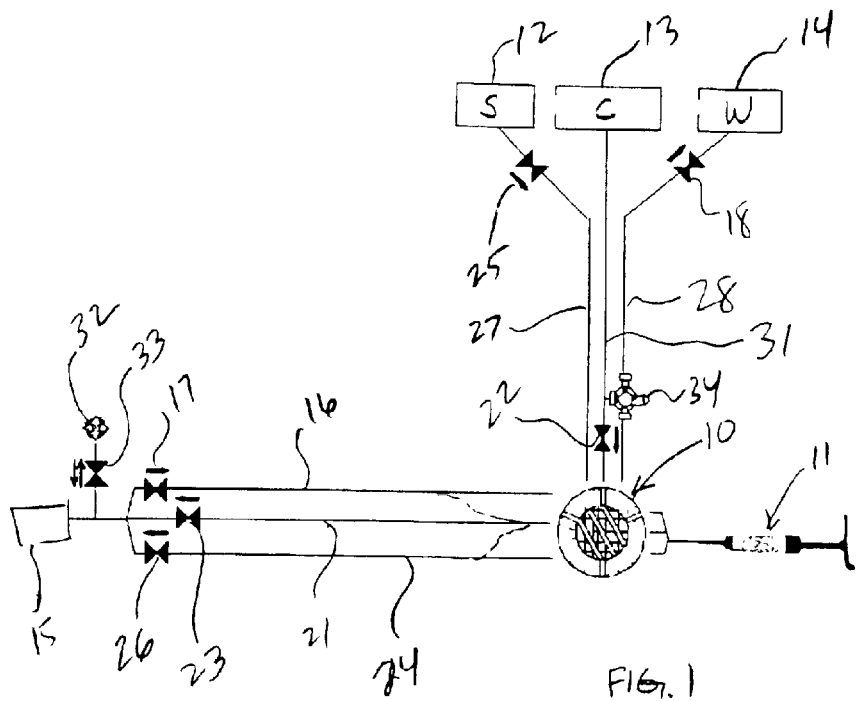
FIG. 1 illustrates, schematically, a fluid control valve made in accordance with the disclosure as coupled to a saline supply, contrast supply, waste receptacle, injector, catheter and pressure transducer.

FIG. 1 illustrates a fluid control valve 10 as coupled to injector 11, a saline supply 12, a contrast supply 13, and a waste dump or reservoir 14. The control valve 10 is also coupled to a catheter, shown schematically at 15. In the embodiment illustrated in FIG. 1, three lines couple the control valve 10 to the catheter 15. A waste line 16 equipped with a one-way valve 17 communicates waste fluid from the catheter 15 through the valve 10, through the one-way valve 18 to the waste reservoir 14. The operation of the valve 10, and numerous refinements thereof, will be explained below. The contrast line 21 communicates fluid drawn from the contrast reservoir 13 through the one-way check valve 22, through the valve 10, and through the one-way check valve 23 to the catheter 15. Finally, the saline line 24 communicates saline drawn from the saline reservoir 12 through the one-way check valve 25, to the valve 10, through the one-way check valve 26 to the catheter 15.

The one-way check valve 25 in the saline input line 27 prevents contaminants from being pumped into the fresh saline supply 12. The one-way check valve 18 in the waste output line 28 prevents wastes from the waste dump 14 from being drawn into the fluid control valve 10 and injector 11. The one-way check valve 22 in the contrast input line 31 prevents waste, saline or other contaminants from being injected into the fresh contrast supply 13. The one-way check valve 17 prevents waste in the waste input line 16 from being injected back into the catheter 15. The one-way check valve 23 in the contrast output line 21 prevents saline, waste or other contaminants from contaminating the contrast flowing through the contrast output line 21. The one-way check valve 26 similarly prevents contaminants or waste being drawn from the catheter 15 into the saline output line 24.

A pressure transducer 32 is also coupled to the catheter 15. A two-way, closeable valve 33 can be closed to isolate the pressure transducer 32 during the high pressure injection of saline or contrast into the catheter 15. A stopcock 34 provides a bypass for the contrast input check valve 22 which enables excess contrast to be pumped back into the contrast reservoir 13.

The fluid control valve 10 can be provided in the form of many embodiments, some of which are disclosed at 10a in FIGS. 2–6, 10b in FIGS. 7–9, 10c in FIGS. 10–12, 10d in FIGS. 13–15, 10c in FIGS. 16–18, 10f in FIGS. 19–21, 10g in FIGS. 22–24, 10h in FIGS. 25–27, 10i in FIGS. 28–30 and 10j in FIGS. 31–34.

Figure 2:
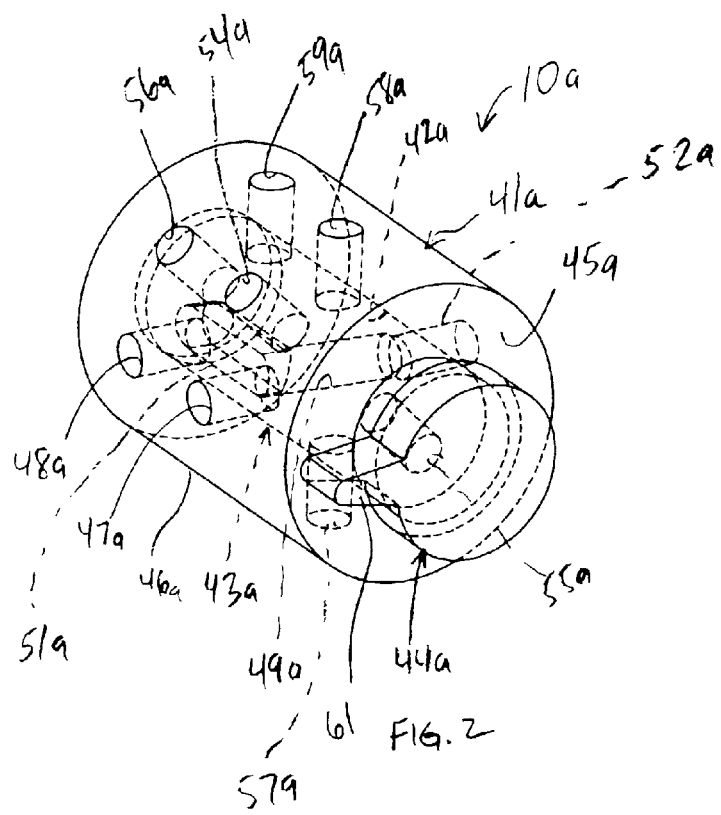
FIG. 2 is a perspective view of a disclosed fluid control valve.
Figure 3:
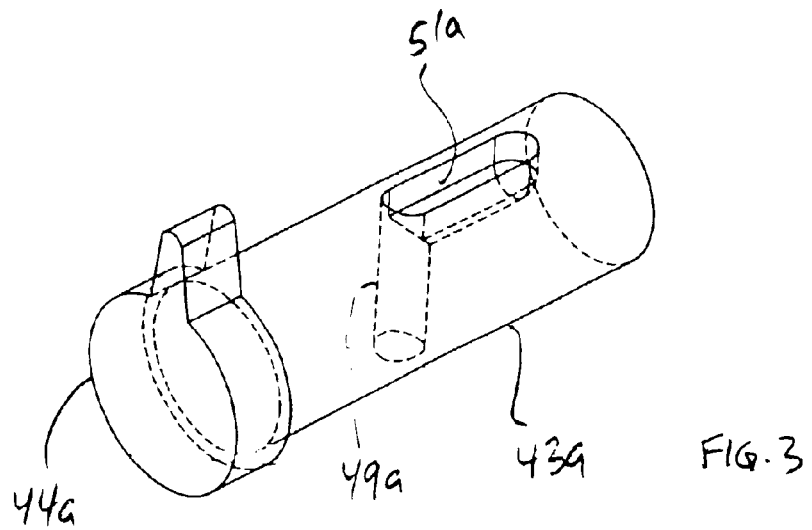
FIG. 3 is a perspective view of the valve stem and handle of the fluid control valve shown in FIG. 2.
Figure 4:
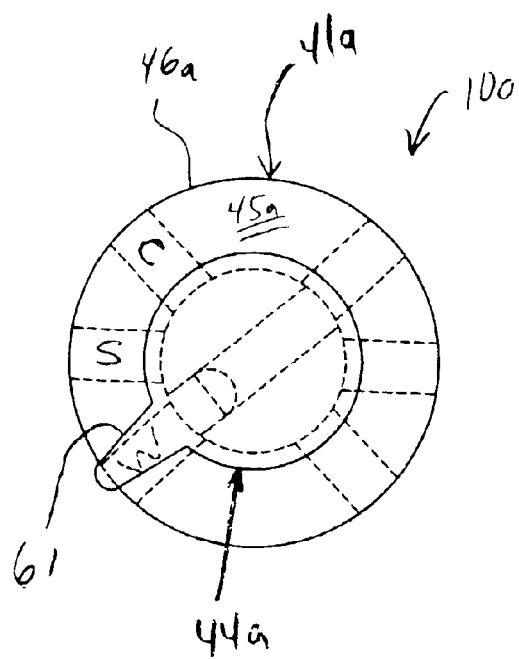
FIG. 4 is an end view of a fluid control valve shown in FIG. 2.

Turning to FIGS. 2–6, the fluid control valve 10a includes a valve body 41a with a cylindrical bore 42a disposed therein. The bore 42a rotatably accommodates a valve stem 43a. An end of the valve stem 43a connected to a handle 44a. As shown in FIG. 4, the handle 44a is rotatable to three positions, preferably marked on the end surface 45a with the designation "W" for waste, "C" for contrast and "S" for saline or injection. In the embodiment 10a shown FIGS. 2–6, the valve body 41a includes nine passages passing from an exterior surface of the valve body 46a, through the valve body 41a to the cylindrical bore 42a. In FIG. 2, the handle 44a and valve stem 43a have been rotated to the waste position (see also FIG. 4). In this position, the waste input passage 47a and the waste output passage 48a are in communication with the connecting passage 49a of the valve stem 43a. Further, the valve 43a includes a linking passage 5 1a which provides communication between the connecting passage 49a, the waste input passage 47a and waste output passage 48a. The connecting passage 49a, in addition to being in alignment with the waste input 47a, is also in alignment with the waste injector passage 52a.

Accordingly, in the position shown in FIG. 2, suction may be applied by the injector 11, thereby drawing waste in from the catheter through the waste input passage 47a, through the connecting passage 49a, through the waste injector passage 52a before outward pressure is applied by the injector 11 thereby injecting the waste back through the waste injector passage 52a, the connecting passage 49a, through the linking passage 51a and out the waste output passage 48a. The waste output passage 48a is connected to a waste output line 28 as shown in FIG. 1. Accordingly, the waste passes through the one-way check valve 18 and into the waste dump 14 as shown in FIG. 1. The one-way check valve 17 in the waste input line 16, which is connected to the waste input passage 47a, prevents waste from reentering the waste input line 16 and thereby forcing the waste down the linking passage 51a and out the waste output passage 48a. The configuration of the connecting passage 49a and linking passage 5 1a is further illustrated in FIG. 3.

Figure 5:
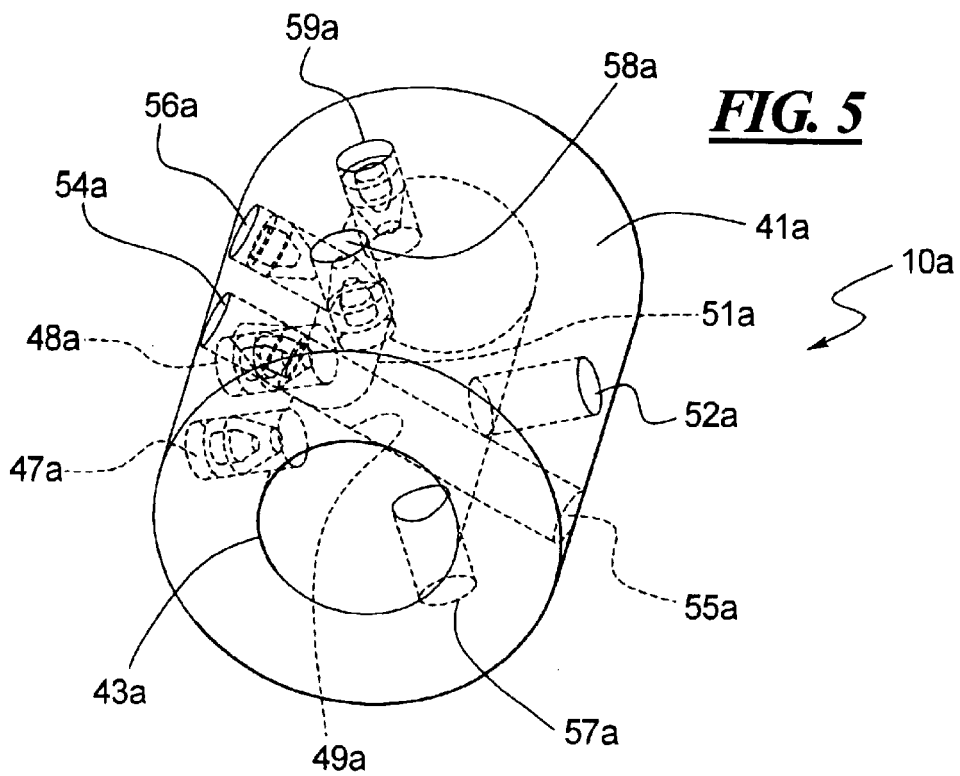
FIG. 5 is another perspective view of the fluid control valve shown in FIG. 2, but in a different rotational position and with the handle removed.
Figure 6:
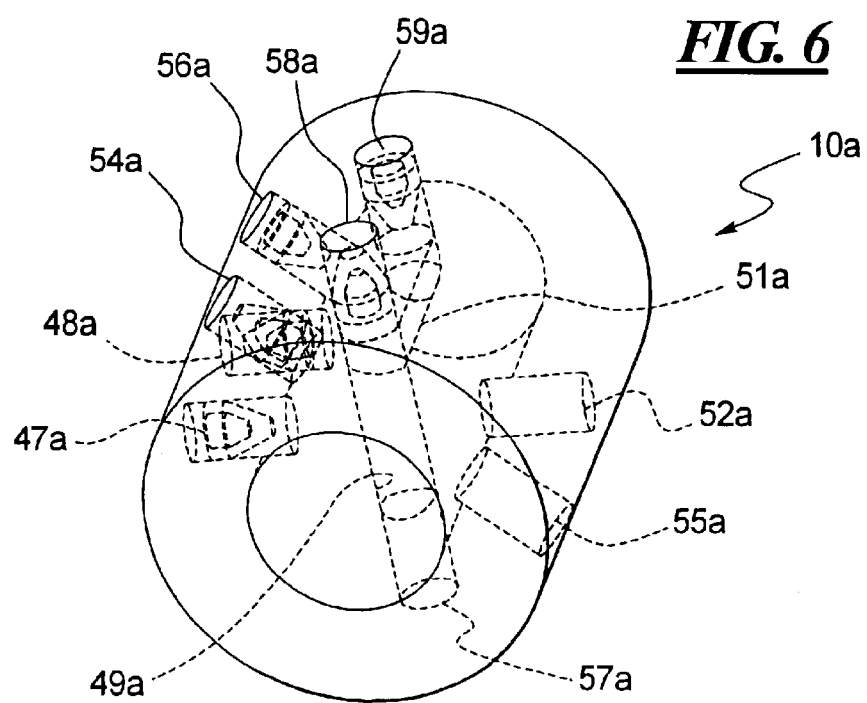
FIG. 6 is another perspective view of the fluid control valve shown in FIG. 2, but in yet another different rotational position and with the handle removed.

Turning to FIGS. 5 and 6, it will be noted that the handle 44a has been removed for clarity. In FIG. 5, the handle 44a and valve stem 43a has been rotated clockwise so that the connecting passage 49a is in alignment with the saline output passage 54a, on one side of the valve body 41a and the saline injector passage 55a. The linking passage 51a extends from the connecting passage 49a to the saline input passage 56a. Accordingly, in the position shown in FIG. 5, suction can be applied by the injector 11 through the saline injector passage 55a, which draws saline from the saline port 12, through the one-way check valve 25, through the saline input passage 56a, through the linking passage 51a and in through the connecting passage 49a. Substantial amounts of saline are not drawn into the valve 10a from the saline output line 24 because of the one-way check valve 26 as shown in FIG. 1. Positive displacement pressure applied by the injector 11 drives saline from the saline injector passage 55a, through the connecting passage 49a, out the saline output passage 54a and down the saline output line 24 before passing through the one-way check valve 26 and into the catheter 15.

Turning to FIG. 6, the handle 44a (not shown in FIG. 6) and the valve stem 43a have been rotated further clockwise so that the connecting passage 49a is in alignment with the contrast injector passage 57a and the contrast output passage 58a. The linking passage 51a connects the connecting passage 49a to the contrast input passage 59a. Thus, in the position shown in FIG. 6, suction applied by the injector 11 draws contrast from the contrast supply 13, through the one-way check valve 26, through the contrast input passage 59a, into the linking passage 51a and into the connecting passage 49a. Then, positive displacement pressure applied by the injector 11, results in expulsion of the contrast fluid from the contrast injector passage 57a, connecting passage 49a and out the contrast output passage 58a and into the contrast output line 21 where the contrast fluid flows through the one-way check valve 23 and into the catheter 15. It will be noted that when the handle is the position shown in FIG. 6, the finger tab 61 will be in alignment with the "C" designator as shown in FIG. 4 and, when the finger tab 61 is in the position shown in FIG. 5, it will be in alignment with the "S" designator shown in FIG. 4.

As best shown in FIGS. 2, 5 and 6, the passages extending through the valve body 41a are arranged in three planes. The waste output passage 48a, the saline input passage 56a and the contrast input passage 59a are arranged in one plane (see FIG. 2). The contrast injector passage 57a, the saline injector passage 55a, the waste injector passage 52a, the contrast output passage 58a, the saline output passage 54a and the waste input passage 47a are also arranged in one plane.

Figure 7:
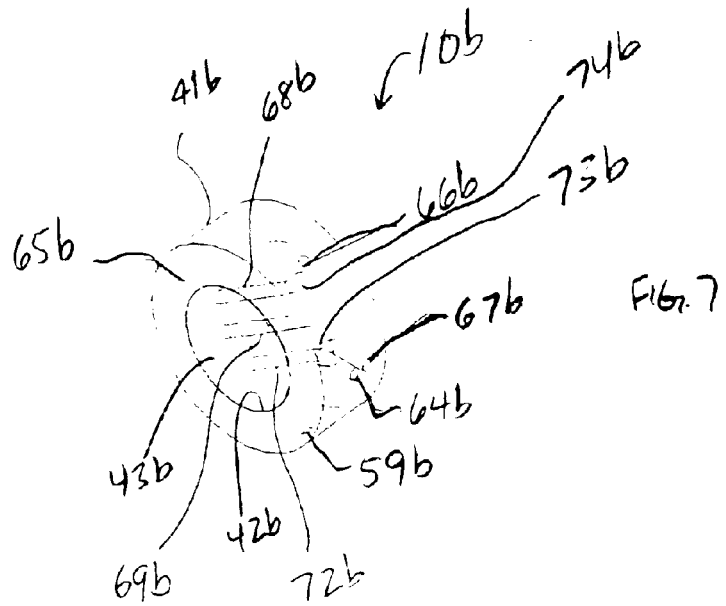
FIG. 7 is a perspective view of yet another fluid control valve in accordance with the disclosure.
Figure 8:
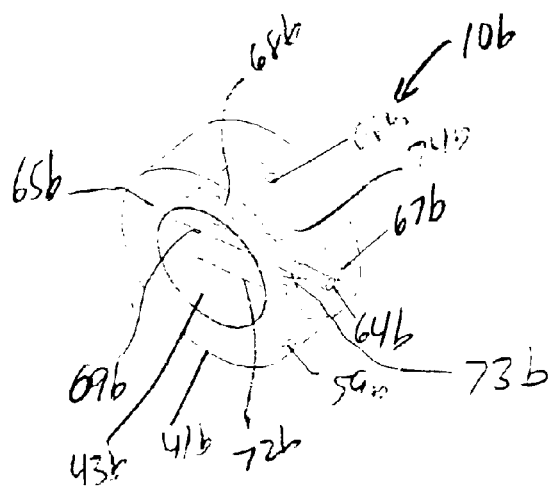
FIG. 8 is a perspective view of the fluid control valve shown in FIG. 7, but in a different rotational position.
Figure 9:
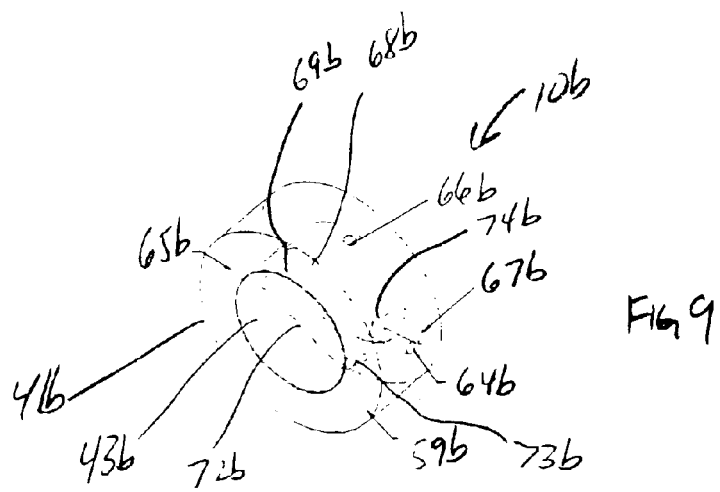
FIG. 9 is another perspective view of the fluid control valve shown in FIG. 7, but in yet another different rotational position.

Turning to FIGS. 7–9, a second fluid control valve 10b is disclosed. Again, a valve body 41b is disclosed with a central bore 42b to accommodate a valve stem 43b. The number of passages passing through the valve body 41b has been reduced by using a plurality of connecting passages through the valve stem 43b as well as two linking passages. Specifically, a single output passage 64b is provided which is connected to the catheter 15. Further, a single injector passage 65b is provided which is connected to the injector 11. A single saline/waste input/output passage 66b is provided which is connected to a y-connection (not shown) which, in turn, is connected to the saline input line 27 and waste output line 28. A contrast input passage 59b is connected to the contrast input line 31. To monitor pressure in the catheter 15, a pressure transducer passage 67b is provided and its use will be discussed below.

Turning to the valve stem 43b (which is connected to a handle 44-not shown) three separate connecting passages are provided. Those connecting passages are a saline/waste connecting passage 68b, an injector connecting passage 69 and a contrast connecting passage 72b. Further, the valve stem 43b includes a first linking passage 73b that extends from the contrast connecting passage 72b and out through the valve stem 43b. The valve stem 43b also includes a second linking passage 74b which extends from the saline/waste connecting passage 68b and out the valve stem 43b.

FIG. 7 shows the valve 10b in the saline/waste rotational position. In the position shown in FIG. 7, the saline/waste connecting passage 68b is in alignment with the injector passage 65b and the saline/waste input/output passage 66b. Thus, suction applied at the injector 11 draws saline through the passage 66b, into the saline/waste connecting passage 68b, through the injector passage 65b and into the injector 11.

To inject the saline into the catheter 15, the valve stem 43b is rotated to the position shown in FIG. 8. Specifically, in FIG. 8, the injector connecting passage 69b has been rotated so that it is in alignment with the injector passage 65b and output passage 64b. Saline may now be injected through the injector connecting passage 69b, through the output passage 64b to the catheter 15. It will be noted that the pressure transducer passage 67b is isolated in the position shown in FIG. 8. Thus, the relatively high pressure event of injecting saline into the catheter 15 is not monitored by the pressure transducer. Thus, the pressure transducer is protected from the high pressure event. In contrast, returning to FIG. 7, catheter pressure can be monitored in the saline/waste position shown in FIG. 7 as the pressure transducer passage 67b is in communication with the output passage 64b (which is connected to the catheter 15) by the first linking passage 73b. No linking passage links the pressure transducer passage 67b through the output passage 64b in the injection position shown in FIG. 8.

In the event waste material needs to be withdrawn from the catheter, in the position shown in FIG. 8, suction is applied at the injector passage 65b to draw waste material through the output passage 64b and injector connection passage 69b and into the injector 11. Then, the valve is rotated to the saline/waste position shown in FIG. 7, and the waste material is expelled through the injector passage 65b, through the saline/waste connecting passage 68b, through the saline/waste input/output passage 66b and into the waste output line 28.

To withdraw contrast from the contrast supply 13, the valve stem 42b is rotated to the position shown in FIG. 9. Specifically, the contrast connection passage 72b is moved into a position where it is in alignment with the injector passage 65b and the contrast input passage 59b. Contrast may now be drawn from the contrast reservoir 13, through the contrast input line 31, through the contrast input passage 59b, through the contrast connecting passage 72b, through the injector passage 65b and into the injector 11. To inject the contrast into the catheter 15, the valve stem 43b is rotated to the position in FIG. 8. While the injector 11 is loaded with contrast (FIG. 9) the pressure in the catheter may be monitored as the output passage 64b is linked to the pressure transducer passage 67b by the second linking passage 74b.

Figure 10:
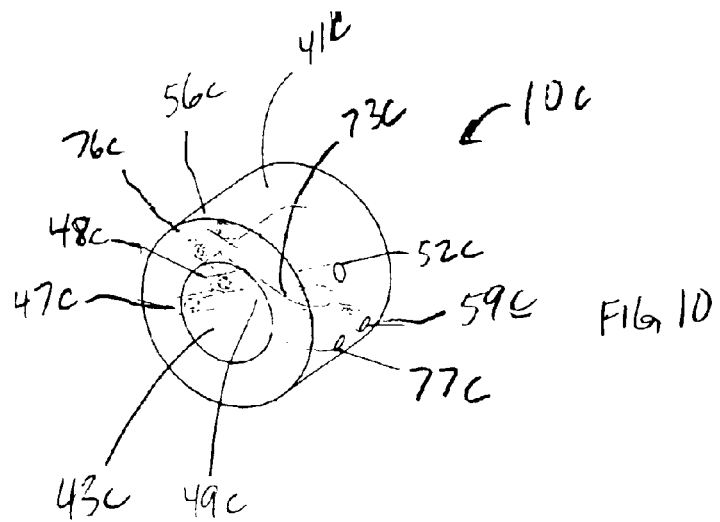
FIG. 10 is a perspective view of yet another disclosed fluid control valve.
Figure 11:
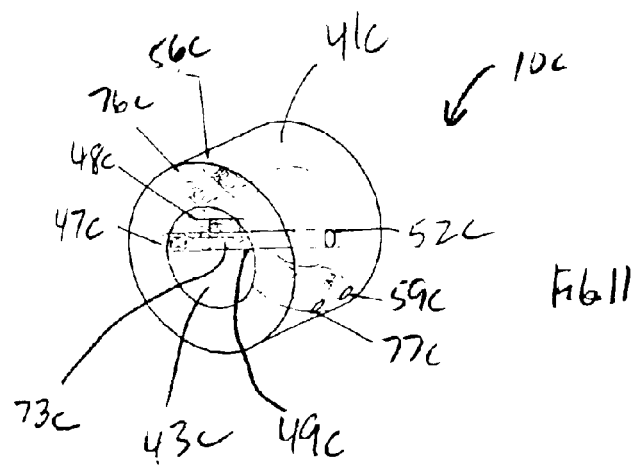
FIG. 11 is another perspective view of a fluid control valve shown in FIG. 10, but in a different rotational position.
Figure 12:
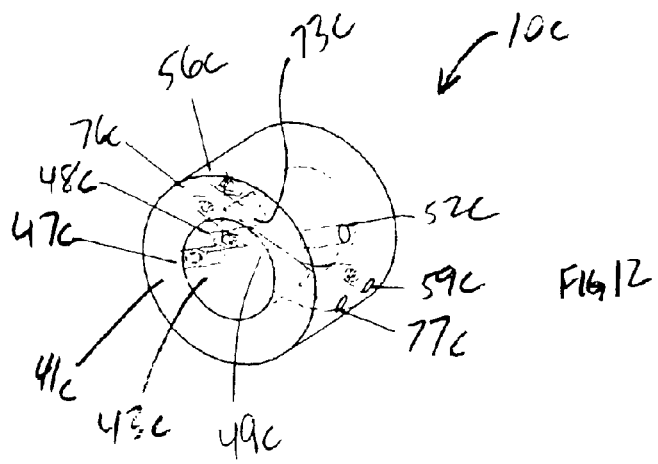
FIG. 12 is another perspective view of the fluid control valve shown in FIG. 10, but in yet another different rotational position.

Turning to the embodiment 10c illustrated in FIGS. 10–12, the passages through the valve body 41c are arranged in two planes. Specifically, a separate waste input passage 47c is provided which is connected to the catheter 15. A separate waste output passage 48c is connected to the waste output line 28. A waste injector passage 52c is arranged on the same plane as the waste input passage 47c and waste output passage 48c, but in a diametrically opposed position in the valve body 41c. A saline input passage 56c is arranged in a coplanar relationship with a combination contrast/saline output passage 76c. In a diametrically opposed but coplanar relationship with the combination contrast/saline output passage 76c and saline input passage 56c are a combination contrast/saline injector passage 77c and a contrast input passage 59c.

In the position shown in FIG. 10, suction is applied by the injector 11 thereby causing contrast to be drawn through the contrast input passage 59c, through the linking passage 73c, through the combination contrast/saline injector passage 77c and into the injector 11. A one-way check valve in the catheter line prevents substantial amounts of fluid from being drawn in through the combination contrast/saline output passage 76c. Contrast may then be injected from the injector 11 by applying positive displacement pressure which forces the contrast fluid through the injector passage 77c, through the connecting passage 49c, out the output passage 76c to the catheter 15. The one-way check valve 22 and the contrast line 31 prevents substantial amounts of contrast fluid from reentering the contrast line 31.

To remove waste material from the catheter, the valve stem 43c was rotated to the position shown in FIG. 11. In this position, waste is drawn in from the catheter 15 through the waste input passage 47c, through the connecting passage 49c, through the waste injector passage 52c through the injector 11. The one-way check valve 18 in the waste line 28 prevents substantial amounts of waste being drawn in through the waste output passage 48c and through the linking passage 73c. To expel the waste, positive displacement pressure is provided by the injector 11 which expels waste through the connecting passage 49c, through the linking passage 73c and out the waste output passage 48c to the waste line 28. The one-way check valve 17 in the waste line 16 connected to the catheter 15 prevents substantial amounts of waste from reentering the waste input line 16 which is connected to the waste input passage 47c.

To withdraw saline from the saline supply 12 and to inject saline to the catheter 15, the valve stem 43c is rotated to the position shown in FIG. 12. Specifically, the connecting passage 49c is now in alignment with the combination contrast/saline output passage 76c. The linking passage 73c provides communication between the connecting passage 49c and the saline input passage 56c. Saline is drawn in through the combination contrast/saline injector passage 77c into the injector 11. The one-way check valve 26 in the saline output line 24 prevents substantial amounts of saline in the line 24 from being drawn into the injector 11. To inject the first saline into the catheter 15, positive displacement pressure is applied by the injector 11 which expels the saline through the injector passage 77c, through the connecting passage 49c and out the combination contrast/saline output passage 76c to the saline output line 24 where it passes through the one-way check valve 26 to the catheter 15.

Figure 13:
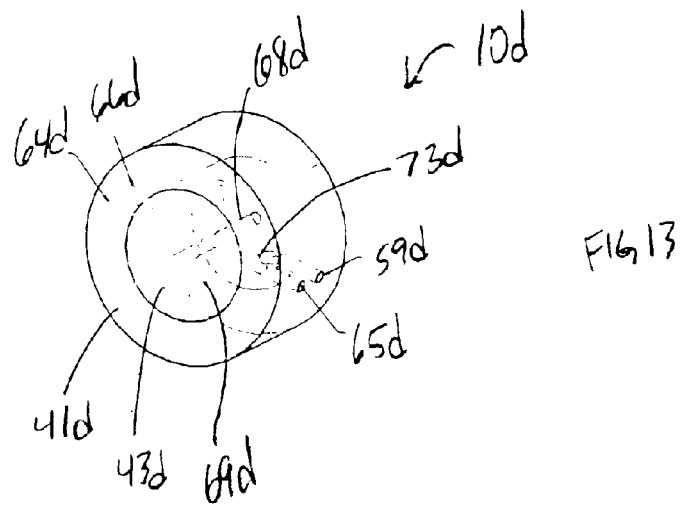
FIG. 13 is a perspective view of yet another fluid control valve in accordance with the disclosure.
Figure 14:
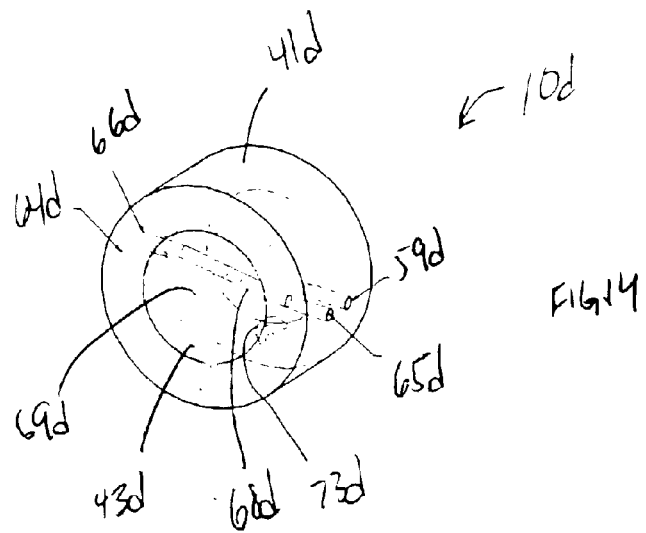
FIG. 14 is another perspective view of the fluid control valve shown in FIG. 13, but in a different rotational position.
Figure 15:
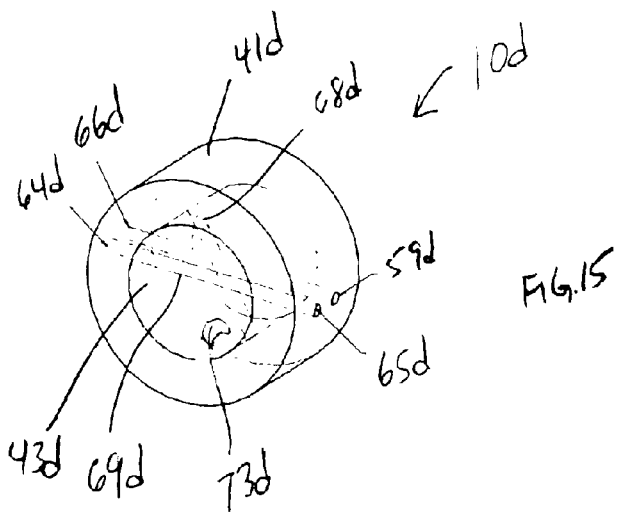
FIG. 15 is another perspective view of the fluid control valve shown in FIG. 13, but in yet another different rotational position.

Turning to the embodiment 10d shown in FIGS. 13–15, it will be noted that the passages through the valve body 41d are arranged in a single plane. Specifically, a single output passage 64d is provided in a coplanar relationship with a combination saline/waste input/output passage 66d. Diametrically opposed from these two passages are an injector passage 65d and a contrast input passage 59d. Two connecting passages extend through the valve stem 43d. Those connecting passages include a saline/waste connecting passage 68d and an injector connecting passage 69d. In the position shown in FIG. 13, the contrast input passage 59d is linked to the injector passage 65d by a linking passage 73d. Contrast may be drawn in from the contrast reservoir 13, through the contrast line 31, through the one-way check valve 22, through the contrast input passage 59d, through the linking passage 73d, through the injector passage 65d to the injector 11. To inject the contrast into the catheter 15, the valve stem 43d is rotated to the position shown in FIG. 15. In this position, the injector connecting passage 69d is in alignment with the output passage 64d which is connected to the catheter by way of a contrast line 21 or other multiple connection line. Pressure applied by the injector 11 forces the contrast fluid through the injector passage 65d, through the injector connecting passage 69d, and out the output passage 64d to the catheter 15. It will be known that in the position shown in FIG. 15, the linking passage 73d has been rotated to an isolated position.

To draw saline in from the saline supply 12, the valve stem 43d is rotated to the position shown in FIG. 14. Specifically, the combination saline/waste connecting passage 68d is rotated into a position where it is aligned with the combination saline/waste input/output 66d and the injector passage 65d. Saline may be drawn in from the reservoir 12, through the line 27, through the input passage 66d, through the saline/waste connecting passage 68, through the injector passage 65d to the injector 11. To inject the saline into the catheter 15, the valve stem 43 is returned to the position shown in FIG. 15. To withdraw waste from the catheter, the valve stem 43d is also rotated to the position shown in FIG. 15.

Figure 16:
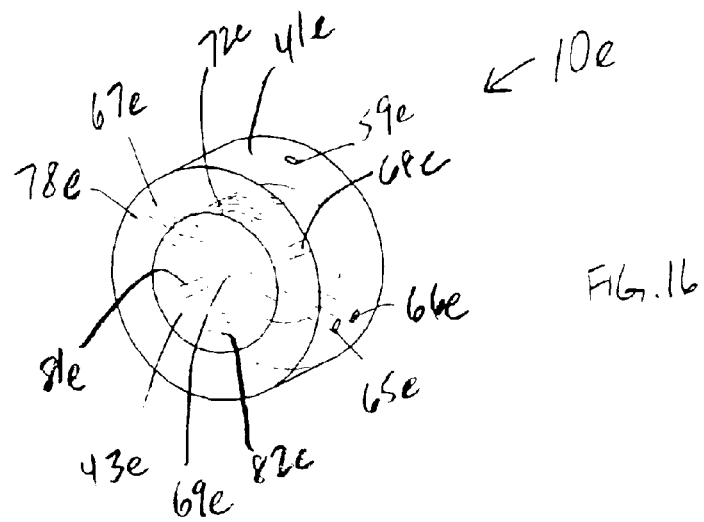
FIG. 16 is a perspective view of yet another fluid control valve in accordance with the disclosure.
Figure 17:
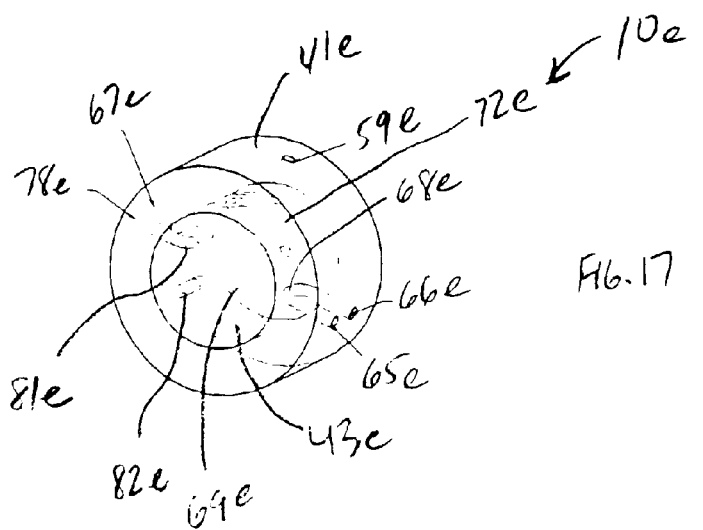
FIG. 17 is a perspective view of the fluid control valve shown in FIG. 16, but in a different rotational position.
Figure 18:
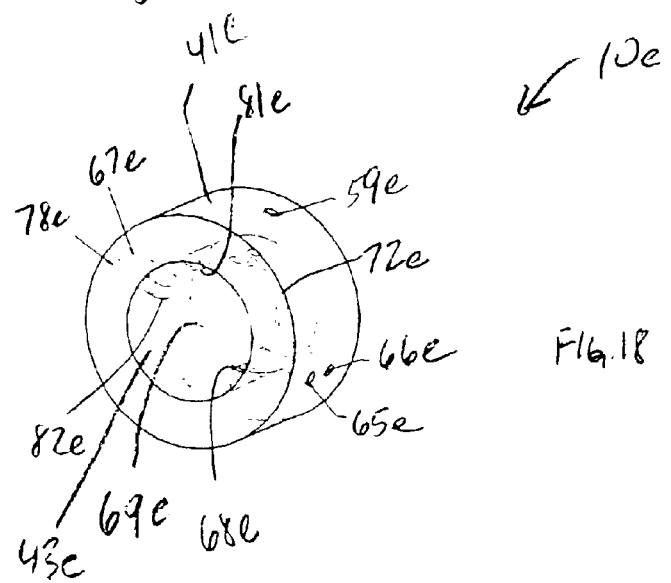
FIG. 18 is another perspective view of the fluid control valve shown in FIG. 16, but in yet another different rotational position.
Figure 31:
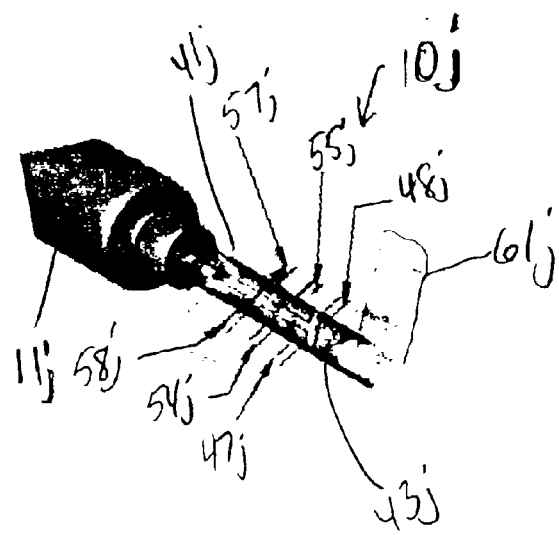
FIG. 31 is partial perspective/sectional view illustrating yet another control valve in accordance with the disclosure as connected to a catheter.

Turning to the embodiment 10e shown in FIGS. 16–18, a single combination input/output passage 78e is provided. Adjacent to the combination input/output passage 78e is a pressure transducer passage 67e. Diametrically opposed from the output passage 78e and pressure transducer passage 67e are the injector passage 65e and combination saline/waste input/output passage 66e. The valve stem 43e includes an injector connecting passage 69e, a contrast connecting passage 72e, a saline/waste connecting passage 68e and two pressure transducer connecting passages 81e, 82e. A contrast input passage is shown at 59e.

In the position shown in FIG. 16, material may be injected from the injector 11 to the catheter 15. Specifically, the injector connecting passage 69e is alignment with the injector passage 65e and the combination input/output passage 78e. In this position, the pressure transducer passage 67e is isolated to avoid the high pressure event. Also in FIG. 16, waste from the catheter may be drawn in through the combination input/output passage 78e, through the injector connecting passage 69e, through the injector passage 65e to the injector 11. To expel the waste from the injector 11, the valve stem 43e is rotated to the position shown in FIG. 17. The waste is expelled through the injector passage 65e, through the saline/waste connecting passage 68e and out the saline/waste input/output passage 66e. A one-way check valve 25 and the saline line 27 prevents waste from entering the saline line 27. In the position shown in FIG. 17, the injector 11 may also be loaded with saline. Saline is drawn in through the saline/waste input/output passage 66e, through the saline/waste connecting passage 68e and through the injector passage 65e. To inject the saline to the catheter, the valve stem 43e is returned to the position shown in FIG. 16. During the saline loading and waste expulsion procedures described for FIG. 17, it will be noted that the pressure transducer connecting passage 81e provides communication between the input/output passage 78e and the pressure transducer passage 67e. Thus, the pressure in the catheter can be monitored during both of these procedures.

To load the injector with contrast, the valve stem 43e is rotated to the position shown in FIG. 18. Contrast is drawn in through the contrast input passage 59e, through the contrast connecting passage 72e to the injector passage 65e. The second pressure transducer connecting passage 82e provides communication between the catheter by way of the input/output passage 78e and the pressure transducer passage 67e. Thus, pressure in the catheter 15 can also be monitored during the contrast loading procedure. To inject the contrast to the catheter, the valve stem 43e is returned to the position shown in FIG. 16.

Turning to the embodiment 10f shown in FIGS. 19–21, a combination input/output passage 78f is provided in a coplanar relationship with respect to a pressure transducer passage 67f. An injector passage 65f is disposed between a contrast input passage 59f and a saline/waste input/output passage 66f. As shown in FIGS. 19–21, the combination input/output passage 78f, which is connected to the catheter 15, the pressure transducer passage 67f, the contrast input passage 59f, the injector passage 65f and the saline/waste input/output passage 66f are all in a coplanar relationship with respect to each other. The valve stem 43f includes an injector connecting passage 69f, two pressure transducer connecting passages 81f, 82f, a saline connecting passage 83f and a contrast connecting passage 72f. In the position shown in FIG. 19, saline may be loaded into the injector 11 by applying suction through the injector passage 65f which causes saline to flow from the saline supply 12, through the saline line 27 which is connected to the saline/waste input/output passage 66f. The saline flows through the saline connector passage 83f to the injector passage 65f and into the injector 11. To inject to the saline into the catheter 15, the valve stem 43f is rotated to the position in FIG. 21. Similarly, to draw waste in from the catheter 15, the position shown in FIG. 21 is utilized. To expel the waste from the catheter 11, the valve stem 43f is rotated to the position shown in FIG. 19 where the waste is expelled through the combination saline/waste input/output passage 66f. Similarly, to draw waste in from the catheter 15, the position shown in FIG. 21 is utilized. To expel waste from the injector 11, the position shown in FIG. 19 is utilized.

To draw contrast into the injector 11, the position shown in FIG. 20 is utilized. Specifically, contrast is drawn in from the contrast reservoir 13, through the contrast line 28, through the one-way check valve 22 and through the contrast input passage 59f. The contrast proceeds through the contrast connecting passage 72f and through the injector passage 65f to the injector 11. To inject the contrast into the catheter 15, the valve stem 43f is again returned to the position shown in FIG. 21. It will be noted that pressure in the catheter can be monitored during the contrast loading procedure described with respect to FIG. 20 as the pressure transducer connecting passage 81f provides communication between the pressure transducer passage 67f and the input/output passage 78f. Similarly, the pressure in the catheter can be monitored during the saline loading procedure and waste expulsion procedure described above with respect to FIG. 19 as the pressure transducer connecting passage 82f provides communication between the pressure transducer passage 67f and input/output passage 78f. During the injection procedure, as shown in FIG. 21, the pressure transducer passage 67f is isolated.

Turning to the embodiment 10g, illustrated in FIGS. 22–24, the valve stem 43g is equipped with three connecting passages, similar to the embodiment 10b shown in FIGS. 7–9. Specifically, the valve stem 43g includes a saline/waste connecting passage 68g, an injector connecting passage 69g and a contrast connecting passage 72g. The valve body 41g includes an injector passage 65g, a combination saline/waste input/output passage 66g, a combination input/output passage 78g which is connected to the catheter 15, and a contrast input passage 59g. In the position shown in FIG. 22, saline may be loaded into the injector 11 or waste may be expelled from the injector 11, again using the one-way check valves 25, 18 discussed above in FIG. 1. In the position shown in FIG. 23, saline may be injected into the catheter 15 or waste may be drawn in from the catheter 15 to the injector 11. Similarly, in FIG. 23, contrast previously loaded into the injector 11 may be injected into the catheter 15. In FIG. 24, contrast may be loaded into the injector 11 before it is injected into the catheter 15 using the position shown in FIG. 23.

Turning to the embodiment 10h shown in FIGS. 25–27, two pressure transducer passages 67h and 84h are provided. In the injection position shown in FIG. 25, the pressure transducer passages 67h, 84h are isolated. However, when saline is either loaded into the injector 11 or waste is expelled from the injector 11, when the valve stem 43h is in the rotational position shown in FIG. 26, pressure in the catheter 15 may be monitored through the pressure transducer passage 84 by way of the contrast connecting passage 72h which is alignment with the pressure transducer passage 84h and the input/output passage 78h as shown in FIG. 26. Further, when contrast is being loaded into the injector 11 when the valve stem 43h is in the position shown in FIG. 27, pressure in the catheter 15 may be monitored through the pressure transducer passage 57h as the saline/waste connecting passage 68h is in alignment with the pressure transducer passage 67h and input/output passage 78h. Otherwise, the operation of the valve 10h is identical to the operation of the valve 10g illustrated in FIGS. 22–24 and the valve 10b illustrated in FIGS. 7–9 above.

Turning to the embodiment 10i illustrated in FIGS. 28–30, again a valve body 41i is provided with a single injector passage 65i and combination input/output passage 78i which is connected to the catheter 15. A pressure transducer passage 67i is disposed adjacent to the input/output passage 78i. A combination saline/waste input/output passage 66i is disposed in a diametrically opposed relationship with respect to the contrast input passage 59i. An injector connecting passage is provided at 69i and a combination saline/waste/contrast connecting passage is shown at 85i. While the connecting passage 85i is in communication with the injector connecting passage 69i, it will be noted that these two passages may be separate and non-communicative within the valve stem 43i.

In the position shown in FIG. 28, pressure in the catheter 15 may be monitored through the pressure transducer connecting passage or linking passage 81i. Saline may be loaded into the injector 11 by way of the combination saline/waste input/output passage 66i, combination saline/contrast/waste connecting passage 85i and an injector passage 65i. Similarly, in the position shown in FIG. 28, waste may be expelled from the injector 11 as discussed above with respect to other embodiments. FIG. 29 illustrates the injection position whereby saline or contrast may be injected to the catheter 15 or waste may be drawn in from the catheter 15. In the position shown in FIG. 29, it will be noted that the pressure transducer passage 67i is isolated. In the position shown in FIG. 30, contrast may be loaded into the injector 11 by way of the contrast input passage 59i, the connecting passage 85i and the injector passage 65i. A second linking or pressure transducer connecting passage 82i is provided so that the pressure in the catheter can be monitored during the contrast loading procedure.

Turning to the embodiment 10j illustrated in FIGS. 31–34, a valve body 41j is mounted directly to an injector 11. The valve stem 43j includes a separate contrast output passage 58j, a separate saline output passage 54j and a separate waste input passage 47j. Diametrically opposed from these passages are the contrast injector passage 57j, the saline injector passage 55j and the waste output passage 48j. A handle 61j is connected to the valve stem 43j.

As best illustrated in FIG. 34, the connecting passage 49j extends axially along the valve stem 43j. Three linking passages are provided which extend transversely across the connecting passage 49j. Those linking passages are a contrast linking passage 91j, a saline linking passage 92j and a waste linking passage 93j. Returning to FIG. 31, it will be noted that the valve stem 43j has been rotated so that the contrast linking passage 91j is in registry with both the contrast output passage 58j and contrast injector passage 57j. In this position, the injector 11j may be loaded with contrast through the contrast injector passage 47j and connecting passage 49j. Contrast may then be injected into the catheter 15 through the connecting passage 49j, contrast linking passage 91j and contrast output passage 58j. Again, the one-way check valve 22 discussed above in FIG. 1 prevents substantial amounts of contrast from reentering the contrast line 31 during the contrast injection process. Similarly, if a separate contrast line 21 is provided to the catheter 15, the check valve 23 prevents substantial amounts of contrast or contaminant from being drawn in through the line 21 during the contrast loading procedure.

Figure 32:
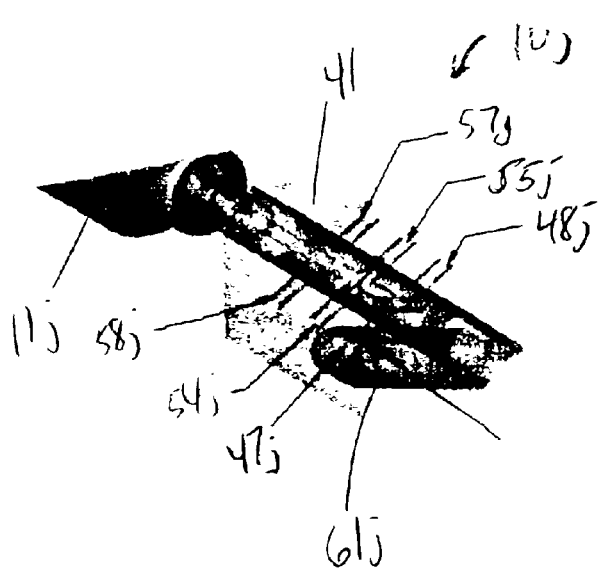
FIG. 32 is another perspective/sectional view of the fluid control valve shown in FIG. 31, but in a different rotational position.

Turning to FIG. 32, the valve stem 43j has been rotated so that the saline linking passage 92j is in registry with the saline input passage 55j and saline output passage 54j. In this position, saline may be drawn into the injector 11j through the saline input passage 55j, saline linking passage 92j; and connection passage 49j. A one-way check valve 26 in a saline line 24 as illustrated in FIG. 1 prevents material from being drawn in from the catheter 15 during this saline loading procedure. To inject the saline into the catheter 15, saline is pumped from the injector 11, through the connecting passage 49j, saline linking passage 92j and out the saline output passage 54j. The one-way check valve 25 and the saline supply line 27 prevents substantial amounts of saline from reentering the line 27 or the saline reservoir 12.

Figure 33:
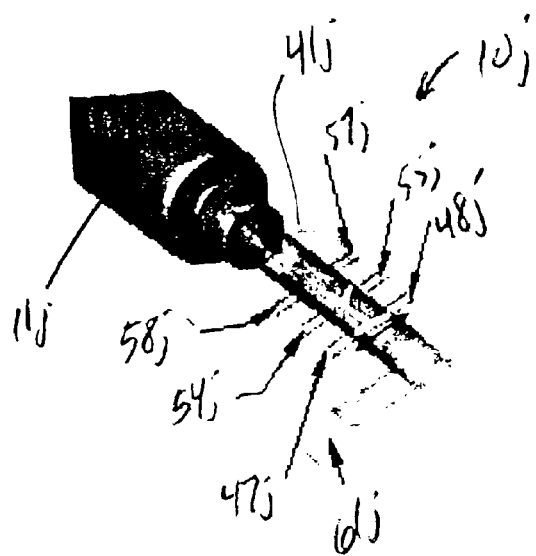
FIG. 33 is another perspective/sectional view of fluid control valve shown in FIG. 31, but in yet another different rotational position.

In FIG. 33, waste may be drawn in from the catheter 15 because the valve stem 43j has been rotated so that the waste linking passage 93j is in registry with the waste output passage 48j and waste input passage 47j, waste linking passage 93j and connecting passage 49j. Suction applied by the injector 11j draws waste in from the catheter 15 through the waste input passage 47j. Waste is expelled out through the connecting passage 49j, waste linking passage 93j and waste output passage 48j by providing positive displacement pressure from the injector 11j. Again, one-way check valves 17 and 18 as discussed above in FIG. 1 prevents substantial amounts of waste from flowing in the wrong direction.

Accordingly, a number of embodiments have been disclosed which provide multiple fluid flow configurations utilizing a single handle. The multiple stopcock handles required by prior art manifolds are no longer necessary. The embodiments disclosed herein are easier to manipulate by the physician and, because there are fewer moving parts, the flow control valves discussed herein are easier and cheaper to manufacture. It will be noted that the number of lines connecting to the catheter as illustrated in FIG. 1 may be reduced and the check valves may be rearranged.

Those skilled in the art will recognize that changes may be made in form and detail without departing from the spirit and scope of this disclosure. As such, it is intended that the foregoing detailed description be regarded as illustrative rather than limiting and it is the following claims, including all equivalents thereof, which are intended to define the scope of the invention.

What is claimed is:

1. A fluid control valve for controlling fluid flow between a catheter, a saline supply, a waste dump, a contrast supply and an injector, the control valve comprising:

a valve body comprising a cylindrical bore and an outer surface, the valve body further comprising at least seven passages providing communication between the cylindrical bore and the outer surface, the at least seven passages comprising a saline output passage connected to the catheter, a contrast output passage connected to the catheter, a waste output passage connected to the waste dump, a contrast input passage connected to the contrast supply, a saline input passage connected to a saline supply, a waste input passage connected to the catheter, and at least one injector passage connected to the injector, a cylindrical valve stem rotably received in the cylindrical bore, the valve stem having a central axis, the valve stem further comprising at least one connecting passage extending through the valve stem, the at least one connecting passage selectively connecting the at least one injector passage to at least one of the saline output passage, the waste input passage or the contrast output passage depending upon a rotational position of the valve stem, the valve stem further comprising a linking passage connecting the saline input passage to the connecting passage, the waste output passage to the connecting passage or the contrast input passage to the connecting passage depending upon the rotational position of the valve stem, the valve stem being rotatable within the cylindrical bore to at least three rotational positions including a contrast position where the connecting passage of the valve stem provides communication between the at least one injector passage and the contrast output passage and the linking passage provides communication between the connecting passage and the contrast input passage, a saline position where the connecting passage provides communication between the injector passage and the saline output passage and the linking passage provides communication between the connecting passage and the saline input passage and a waste position where the connecting passage provides communication between the injector passage and the waste input passage and the linking passage provides communication between the connecting passage and the waste output passage.

2. The control valve of claim 1 wherein the at least one injector passage comprises a contrast injector passage, a saline injector passage and a waste injector passage, the linking passage extending from the connecting passage axially along the valve stem and out through the valve stem, in the contrast position, the connecting passage providing communication between the contrast injector passage and the contrast output passage, the linking passage providing communication between the contrast input passage and the connecting passage, in the saline position, the connecting passage providing communication between the saline injector passage and the saline output passage, the linking passage providing communication between the connecting passage and saline input passage, in the waste position, the connecting passage providing communication between the waste input passage and the waste injector passage, the linking passage providing communication between the connecting passage and the waste output passage.

3. The control valve of claim 2 wherein waste input passage is connected to a waste input line which connects the waste input passage to the catheter, the waste input line comprising a one-way check valve permitting flow from the catheter to the waste input passage and not vice versa, the saline output passage is connected to a saline output line which connects the saline output passage to the catheter, the saline output line comprising a one-way check valve permitting flow from the saline output passage to the catheter and not vice versa, the contrast output passage is connected to a contrast output line which connects the contrast output passage to the catheter, the contrast output line comprising a one-way check valve permitting flow from the contrast output passage to the catheter and not vice versa.

4. The control valve of claim 2 wherein the saline input passage is connected to a saline input line which connects the saline input passage to the saline supply, the saline input line comprising a one-way check valve permitting flow from the saline supply to the saline input passage and not vice versa, the contrast input passage is connected to a contrast input line which connects the contrast input passage to the contrast supply, the contrast input line comprising a one-way check valve permitting flow from the contrast supply to the contrast input passage and not vice versa, the waste output passage is connected to a waste output line which connects the waste output passage to the waste dump, the waste output line comprising a one-way check valve permitting flow from the waste output passage to the waste dump and not vice versa.

5. The control valve of claim 1 wherein the at least one injector passage comprises a combination contrast/saline injector passage and a waste injector passage, the linking passage extends from the connecting passage along the valve stem and out through the valve stem, in the contrast position, the connecting passage providing communication between the combination contrast/saline injector passage and the combination contrast output passage, in the contrast position, the linking passage providing communication between the contrast input passage and the connecting passage, in the saline position, the connecting passage providing communication between the combination contrast/saline injector passage and the combination contrast/saline output passage, in the saline position, the linking passage providing communication between the connecting passage and saline input passage, in the waste position, the connecting passage providing communication between the waste input passage and the waste injector passage, in the waste position, in the linking passage providing communication between the connecting passage and the waste output passage.

6. The control valve of claim 5 wherein the saline input passage, the combination contrast/saline output passage, the combination contrast/saline injector passage and the contrast input passage are coplanar.

7. The control valve of claim 5, wherein waste input passage is connected to a waste input line which connects the waste input passage to the catheter, the waste input line comprising a one-way check valve permitting flow from the catheter to the waste input passage and not vice versa, the contrast output passage is connected to a contrast output line which connects the contrast output passage to the catheter, the contrast output line comprising a one-way check valve permitting flow from the contrast output passage to the catheter and not vice versa.

8. The control valve of claim 5 wherein the saline input passage is connected to a saline input line which connects the saline input passage to the saline supply, the saline input line comprising a one-way check valve permitting flow from the saline supply to the saline input passage and not vice versa, the contrast input passage is connected to a contrast input line which connects the contrast input passage to the contrast supply, the contrast input line comprising a one-way check valve permitting flow from the contrast supply to the contrast input passage and not vice versa, the waste output passage is connected to a waste output line which connects the waste output passage to the waste dump, the waste output line comprising a one-way check valve permitting flow from the waste output passage to the waste dump and not vice versa.

9. The control valve of claim 1 wherein the contrast output passage and a saline output passage are connected to the catheter, the linking passage of the valve stem extending axially along the valve stem, in the contrast position, the connecting and linking passages providing communication between the injector passage, the contrast input passage and the contrast output passage, in the contrast position, the saline and waste output passages are blocked by the valve stem, in the injection position, the connecting and linking passages providing communication between the injector passage, the saline output passage, and the saline input passage, in the injection position, the contrast and waste linking passages are blocked by the valve stem, in the waste position, the connecting and linking passages providing communication between the injector passage, the waste input passage and the waste output passage, in the waste position, the saline and contrast output passages are blocked by the valve stem.

10. The control valve of claim 9 wherein waste input passage is connected to a waste input line which connects the waste input passage to the catheter, the waste input line comprising a one-way check valve permitting flow from the catheter to the waste input passage and not vice versa, the saline output passage is connected to a saline output line which connects the saline output passage to the catheter, the saline output line comprising a one-way check valve permitting flow from the saline output passage to the catheter and not vice versa, the contrast output passage is connected to a contrast output line which connects the contrast output passage to the catheter, the contrast output line comprising a one-way check valve permitting flow from the contrast output passage to the catheter and not vice versa.

11. The control valve of claim 9 wherein the saline input passage is connected to a saline input line which connects the saline input passage to the saline supply, the saline input line comprising a one-way check valve permitting flow from the saline supply to the saline input passage and not vice versa, the contrast input passage is connected to a contrast input line which connects the contrast input passage to the contrast supply, the contrast input line comprising a one-way check valve permitting flow from the contrast supply to the contrast input passage and not vice versa, the waste output passage is connected to a waste output line which connects the waste output passage to the waste dump, the waste output line comprising a one-way check valve permitting flow from the waste output passage to the waste dump and not vice versa.

* * * * *